(12) United States Patent
Rohrwasser et al.

(10) Patent No.: US 6,177,252 B1
(45) Date of Patent: Jan. 23, 2001

(54) METHOD TO DETERMINE PREDISPOSITION TO HYPERTENSION

(75) Inventors: Andreas Rohrwasser; Jean-Marc Lalouel, both of Salt Lake City, UT (US)

(73) Assignee: University of Utah Research Foundation, Salt Lake City, UT (US)

( * ) Notice: Under 35 U.S.C. 154(b), the term of this patent shall be extended for 0 days.

(21) Appl. No.: 09/384,212

(22) Filed: Aug. 27, 1999

(51) Int. Cl.⁷ ............................. C12Q 1/68; C07H 21/04
(52) U.S. Cl. ...................... 435/6; 536/23.1; 536/24.3; 536/24.31
(58) Field of Search ............................... 435/6; 536/23.1, 536/24.3, 24.31, 23.5, 91.2

(56) References Cited

U.S. PATENT DOCUMENTS

| | | | |
|---|---|---|---|
| 5,374,525 | * 12/1994 | Lalouel et al. ........................... | 435/6 |
| 5,589,584 | * 12/1996 | Lalouel et al. ........................... | 435/6 |
| 5,763,168 | *  6/1998 | Lalouel et al. ........................... | 435/6 |
| 5,998,145 | * 12/1999 | Lalouel et al. ........................... | 435/6 |

OTHER PUBLICATIONS

Morgan et al. "DNA polymorphisms and linkage disequilibrium in the AGT gene" Human Genetics, 98: pp. 194–198, 1996.*

Hegele et al. "A polymorphism of the AGT gene associated with variation in blood pressure in a genetic isolate" Circulation. vol. 90, pp. 2207–2212, 1994.*

Fukamizu et al "Structure and Expression of the human AGT gene" J. of Biological Chemistry, vol. 265, pp. 7576–7582, 1990.*

* cited by examiner

Primary Examiner—Lisa B. Arthur
Assistant Examiner—Jeanine Goldberg
(74) Attorney, Agent, or Firm—Rothwell, Figg, Ernst & Manbeck, P.C.

(57) ABSTRACT

The T/C(67) AGT gene variant and the association of the molecular variant C(67) with predisposition of an individual to hypertension are disclosed. The determination of this association enables the screening of persons to identify the severity of hypertension or the severity of the risk of a predisposition to high blood pressure.

10 Claims, No Drawings

METHOD TO DETERMINE PREDISPOSITION TO HYPERTENSION

This invention was made with Government support under Grant Nos. HL24855 and HL45325, awarded by the National Institutes of Health, Bethesda, Md. The United States Government has certain rights in the invention.

BACKGROUND OF THE INVENTION

The present invention relates to molecular variants of the angiotensinogen gene. The present invention further relates to the diagnosis of these variants for the determination of a predisposition to hypertension, the determination of the prognosis of the predisposition to hypertension, and the management of hypertension.

The publications and other materials used herein to illuminate the background of the invention, or provide additional details respecting the practice, are incorporated by reference herein, and for convenience are respectively grouped in the appended List of References.

Hypertension is a leading cause of human cardiovascular morbidity and mortality, with a prevalence rate of 25–30% of the adult Caucasian population of the United States (JNC Report, (1985). The primary determinants of essential hypertension, which represents 95% of the hypertensive population, have not been elucidated in spite of numerous investigations undertaken to clarify the various mechanisms involved in the regulation of blood pressure. Studies of large populations of both twins and adoptive siblings, in providing concordant evidence for strong genetic components in the regulation of blood pressure (Ward (1990)), have suggested that molecular determinants contribute to the pathogenesis of hypertension.

Among a number of factors for regulating blood pressure, the renin-angiotensin system plays an important role in salt-water homeostasis and the maintenance of vascular tone; stimulation or inhibition of this system respectively raises or lowers blood pressure (Hall et al. (1990)), and may be involved in the etiology of hypertension. The renin-angiotensin system includes the enzymes renin and angiotensin-converting enzyme and the protein angiotensinogen (AGT). Angiotensinogen is the specific substrate of renin, an aspartyl protease. The structure of the AGT gene has been characterized (Gaillard et al. (1989); Fukamizu et al. (1990)).

Plasma angiotensinogen is primarily synthesized in the liver under the positive control of estrogens, glucocorticoids, thyroid hormones, and angiotensin II (Clauser et al.(1989)) and secreted through the constitutive pathway. Cleavage of the amino-terminal segment of angiotensinogen by resin releases a decapeptide prohormone, angiotensin-I, which is further processed to the active octapeptide angiotensin II by the dipeptidyl carboxypeptidase angiotensin-converting enzyme (ACE). Cleavage of angiotensinogen by renin is the rate-limiting step in the activation of the renin angiotensin system (Sealey et al. (1990)). Several observations point to a direct relationship between plasma angiotensinogen concentration and blood pressure: (1) a direct positive correlation (Walker et al. (1979)); (2) high concentrations of plasma angiotensinogen in hypertensive subjects and in the offspring of hypertensive parents compared to normotensives (Fasola et al. (1968)); (3) association of increased plasma angiotensinogen with higher blood pressure in offspring with contrasted parental predisposition to hypertension (Watt et al. (1992)); (4) decreased or increased blood pressure following administration of angiotensinogen antibodies (Gardes et al. (1982)) or injection of angiotensinogen (Menard et al. (1991)); (5) expression of the angiotensinogen gene in tissues directly involved in blood pressure regulation (Campbell and Habener (1986)); and (6) elevation of blood pressure in transgenic animals overexpressing angiotensinogen (Ohkubo et al. (1990; Kimura et al. (1992)).

The etiological heterogeneity and multifactorial determination which characterize diseases as common as hypertension expose the limitations of the classical genetic arsenal. Definition of phenotype, model of inheritance, optimal familial structures, and candidate-gene vs. general-linkage approaches impose critical strategic choices (Lander et al. (1986; White et al. (1987; Lander et al. (1989; Lalouel (1990; Lathrop et al. (1991)). Analysis by classical likelihood ratio methods in pedigrees is problematic due to the likely heterogeneity and the unknown mode of inheritance of hypertension. While such approaches have some power to detect linkage, their power to exclude linkage appears limited. Alternatively, linkage analysis in affected sib pairs is a robust method which can accommodate heterogeneity and incomplete penetrance, does not require any a priori formulation of the mode of inheritance of the trait and can be used to place upper limits on the potential magnitude of effects exerted on a trait by inheritance at a single locus. (Blackwelder et al. (1985; Suarez et al. (1984)).

Prior studies have it was found that the angiotensinogen gene is involved in the pathogenesis of essential hypertension. The following were found: (1) genetic linkage between essential hypertension and AGT in affected siblings; (2) association between hypertension and certain molecular variants of AGT as revealed by comparison between cases and controls; (3) increased concentrations of plasma angiotensinogen in hypertensive subjects who carry a common variant of AGT strongly associated with hypertension; (4) persons with the most common AGT gene variant exhibited not only raised levels of plasma angiotensinogen but also higher blood pressure; and (5) the most common AGT gene variant was found to be statistically increased in women presenting preeclampsia during pregnancy, a condition occurring in 5–10% of all pregnancies. The association between renin, ACE or AGT and essential hypertension was studied using the affected sib pair method (Bishop et al. (1990)) on populations from Salt Lake City, Utah and Paris, France, as described in further detail in the Examples. Only an association between the AGT gene and hypertension was found. The AGT gene was examined in persons with hypertension, and at least 15 variants have been identified. None of these variants occur in the region of the AGT protein cleaved by either renin or ACE. Identification of the AGT gene as being associated with essential hypertension was confirmed in a population study of healthy subjects and in women presenting preeclampsia during pregnancy. See, e.g., U.S. Pat. Nos. 5,374,525 and 5,763,168, each incorporated herein by reference; U.S. patent application Ser. No. 09/106,216, filed Jun. 29, 1998, incorporated herein by reference; Jeunemaitre et al. (1992); Jeunemaitre et al. (1993); and Jeunemaitre et al. (1997).

According to Gaillard et al. (1989), the human AGT gene contains five exons and four introns which span 13 Kb. The first exon (37 bp) codes for the 5' untranslated region of the mRNA. The second exon codes for the signal peptide and the first 252 amino acids of the mature protein. Exons 3 and 4 are shorter and code for 90 and 48 amino acids, respectively. Exon 5 contains a short coding sequence (62 amino acids) and the 3'-untranslated region. Genbank accession No. AH002594 also sets forth a sequence of the AGT gene as revised on Oct. 30, 1994. The revised sequence moves the start site of transcription one nucleotide 5' of the transcription start site identified in Gaillard et al. (1989). Since polymorphisms described herein and in the prior art have been written with respect to the Gaillard et al. (1989) transcription start site, this nomenclature will also be used herein.

It is an object of the present invention to identify additional AGT polymorphisms associated with hypertension and to utilize such polymorphisms for determining predisposition to hypertension in individuals. Identification of individuals who may be predisposed to hypertension will lead to better management of the disease.

SUMMARY OF THE INVENTION

The present invention relates to identification of additional polymorphisms of the AGT gene associated with human hypertension. The analysis of the AGT gene for these polymorphisms will identify subjects with a genetic predisposition to develop essential hypertension or pregnancy-induced hypertension. The management of hypertension in these subjects could then be more specifically managed, e.g., by dietary sodium restriction, by carefully monitoring blood pressure and treating with conventional drugs, by the administration of renin inhibitors or by the administration of drugs to inhibit the synthesis of AGT. The analysis of the AGT gene is performed by comparing the DNA sequence of an individual's AGT gene with the DNA sequence of the native, non-variant AGT gene. It has been found that an analysis of the AGT gene introns 1, specifically nucleotide position 67 relative to the transcription start site of Gaillard et al. (1989) of the AGT gene sequence described in further detail herein, can be used to determine the predisposition to hypertension. It has further been found that this polymorphism occurs in linkage disequilibrium with the M/T(235), G/A(−6), and other molecular variants, as described in further detail herein. Accordingly, analysis of this polymorphism can be used in place of an analysis of the latter molecular variants.

SUMMARY OF THE SEQUENCE LISTING

SEQ ID NO: 1 sets forth a wild-type cDNA sequence of the AGT gene according to Gaillard et al. (1989). SEQ ID NO: 2 sets forth the corresponding protein sequence for this cDNA sequence. SEQ ID NO: 3 sets for a wild-type DNA sequence beginning with the TATA box and extending into a portion of intron 1. The "a" at nucleotide position 33 corresponds to Gaillard et al.'s (1989) transcription start site. The "c" at nucleotide position 96 corresponds to an additional base found in the AGT gene in the present invention. SEQ ID NO: 4 corresponds to nucleotides 33–130 of SEQ ID NO: 3 and is used herein to refer to T/C(67) polymorphism. SEQ ID NO: 5 is the sequence of intron 1 in accordance with the present invention corresponding to nucleotides 69–130 of SEQ ID NO: 4.

DETAILED DESCRIPTION OF THE INVENTION

The present invention relates to identification of additional polymorphisms of the AGT gene associated with human hypertension. The analysis of the AGT gene for these polymorphisms will identify subjects with a genetic predisposition to develop essential hypertension or pregnancy-induced hypertension. The management of hypertension in these subjects could then be more specifically managed, e.g., by dietary sodium restriction, by carefully monitoring blood pressure and treating with conventional drugs, by the administration of renin inhibitors or by the administration of drugs to inhibit the synthesis of AGT. The analysis of the AGT gene is performed by comparing the DNA sequence of an individual's AGT gene with the DNA sequence of the native, non-variant AGT gene. It has been found that an analysis of the AGT gene intron 1, specifically nucleotide position 67 relative to the transcription start site of Gaillard et al. (1989) of the AGT gene sequence described in further detail herein, can be used to determine the predisposition to hypertension. It has further been found that this polymorphism occurs in linkage disequilibrium with the M/T(235), G/A(−6), and other molecular variants, as described in further detail herein. Accordingly, analysis of this polymorphism can be used in place of an analysis of the latter molecular variants.

As used herein, AGT gene variants are expressed either at the amino acid level, e.g., M/T(235) in which the variant protein contains threonine at amino acid residue 235 instead of methionine, or at the nucleotide level, e.g., G/A(−6) in which the variant gene contains adenine at nucleotide −6 of the 5' sequence, relative to the transcription start site, instead of guanine of the native gene. Several mutations are set forth in U.S. Pat. No. 5,374,525 (which uses the nomenclature M235T, instead of the nomenclature M/T(235) used herein). In accordance with the present invention, the AGT gene variant T/C(67) (cytosine instead of thymine at nucleotide 67 relative to the transcription start site of modified intron 1 as shown in SEQ ID NO: 4) has been found to be associated with hypertension.

Specifically, we have identified a common molecular variant within the first intron of the human AGT gene, characterized by the presence of either thymine (T) or cytosine (C) at nucleotide +67, and thereafter denoted T/C (67). Allele C(67) occurs in very strong association with allele T235, whereas allele T(67) occurs most often with allele M235. We previously reported a similar pattern of association between the M/T(235) and G/A(−6) polymorphisms, with quasi-association of T325 with A(−6) and M235 with G(−6). Consequently, all associations observed with allele T235 extend not only to allele A(−6), as pointed out at the time, but also to allele C(67). Any one of these three polymorphisms can serve as marker of AGT-mediated predisposition to essential hypertension.

Furthermore, any allele at any of these three sites can potentially play a causal role in the relationship between AGT and essential hypertension or preeclampsia. Our experimental data suggest that, just as observed for the A/G(−6) polymorphism, the T/C(67) polymorphism affects (1) specific interactions between AGT promoter and nuclear proteins in vitro, and (2) the transcriptional activity of the AGT promoter when tested through typical reporter assays in cultured cells. As a consequence, all claims previously filed with respect to either M/T325 or G/A(−6) logically extend to T/C(67).

When hypertensive siblings were stratified according to genotypes at residue 235, higher plasma concentrations of angiotensinogen were observed among carriers of M/T(235) (F23.3=14.9, p<0.0001). Again, this result was observed independently in each sample. A correlation between plasma angiotensinogen concentration and blood pressure has already been observed (Walker et al. (1979)). Taken together, these observations suggest a direct involvement of plasma angiotensinogen in the pathogenesis of essential hypertension. This conclusion is further strengthened by finding that the M/T(235) variant was significantly associated not only with raised plasma angiotensinogen concentrations but also with increased blood pressure. See Example 8 of U.S. Pat. No. 5,374,52.

The present invention is corroborated by two additional findings: (1) plasma angiotensinogen was higher in hypertensive subjects and in offspring of hypertensive parents than in normotensives (Fasola et al. (1968)); and (2) in the Four-Corners study, angiotensinogen concentrations were significantly associated with increased blood pressure in the subset most likely to entail a genetic predisposition, namely the high blood pressure offspring of high-blood pressure parents (Watt et al. (1992)). Because the plasma concentration of angiotensinogen is close to the $K_m$ of the enzymatic reaction between renin and angiotensinogen (Gould et al. (1971)), a rise or fall in renin substrate can lead to a parallel change in the formation of angiotensin II (Cain et al. (1971); Menard et al. (1973; Arnal et al. (1991)). Thus, it is conceivable that raised baseline levels could lead to mild overactivity of the renin-angiotensin system, and represent an altered homeostatic setpoint in predisposed individuals. Indeed, long-term administration of angiotensin II at suppressor doses has been shown to elevate blood pressure (Brown et al. (1981)).

Recent studies suggest that not only plasma angiotensinogen, but also local expression in specific tissues, could contribute to blood pressure regulation. Yongue et al. (1991) observed increased expression of angiotensinogen in the anterioventral hypothalamus and in contiguous areas of the brain in SHR rats in comparison to normotensive control WKY rats, but they found no difference in liver expression. A possible role of angiotensinogen in the central nervous system is further supported by experimental overexpression of the AGT gene in transgenic rats: plasma concentrations were raised, but high blood pressure was observed only in a transgenic line displaying proper tissue-specific expression of the transgene in the brain (Kimura et al. (1992)). Furthermore, evidence for local synthesis of the different components of the renin angiotensin system in the kidney has accumulated and an alteration of the regulation of angiotensinogen expression by sodium has been observed in SHR rats (Pratt et al. (1989)).

Without being bound by any theory of action, it is possible that some molecular variants of angiotensinogen, such as those identified or tagged by the variant at residue 235 or the variant at the −6 nucleotide, lead to increased plasma or tissue angiotensinogen as a result of either increased synthetic rate, altered reaction constants with renin, or increased residence time through complex formation with self or with other extracellular proteins. This could lead to a small increase in baseline or in reactive production of angiotensin II, accounting for a slight overreactivity of the renin angiotensin system in response to sodium and environmental stressors. Over decades, this in turn could promote sodium retention as a result of chronic stimulation of aldosterone secretion, vascular hypertrophy and increased peripheral vascular resistance as a result of chronic elevation of angiotensin II formation, or abnormal stimulation of the sympathetic nervous system mediated by enhanced production of angiotensin II in relevant areas of the brain.

The identification of the association between the AGT gene and hypertension permits the screening of individuals to determine a predisposition to hypertension. Those individuals who are identified at risk for the development of the disease may benefit from dietary sodium restriction, can have their blood pressure more closely monitored and be treated at an earlier time in the course of the disease. Such blood pressure monitoring and treatment may be performed using conventional techniques well known in the art.

To identify persons having a predisposition to hypertension, the AGT alleles are screened for mutations. Plasma angiotensinogen levels of persons carrying variants of the AGT gene are then examined to identify those at risk. Any human tissue can be used for testing the DNA. Most simply, blood can be drawn and DNA extracted from the cells of the blood. The AGT alleles are screened for mutations either directly or after cloning the alleles.

The alleles of the AGT gene in an individual to be tested are cloned using conventional techniques. For example, a blood sample is obtained from the individual. The genomic DNA isolated from cells in this sample is partially digested to an average fragment size of approximately 20 kb. Fragments in the range from 18–21 kb are isolated. The resulting fragments are ligated into an appropriate vector. The sequences are then analyzed as described herein.

Alternatively, polymerase chain reactions (PCRs) are performed with primer pairs for the 5' region or the exons of the AGT gene. Examples of such primer pairs are set forth in U.S. Pat. No. 5,374,525 and U.S. patent application Ser. No. 09/106,216. PCRs can also be performed with primer pairs based on any sequence of the normal AGT gene. For example, primer pairs for the large intron can be prepared and utilized. Finally, PCR can also be performed on the mRNA. The amplified products are then analyzed as described herein.

The alleles are tested for the presence of nucleic acid sequence differences from the normal allele by determining the nucleotide sequence of the cloned allele or amplified fragment and comparing it to the nucleotide sequence of the normal allele. Alternatively, there are six well known methods for a more complete, yet still indirect, test for confirming the presence of a predisposing allele:(1) single stranded conformation analysis (SSCA) (Orita et al. (1989)); (2) denaturing gradient gel electrophoresis (DGGE) (Wartell et al. (1990); Sheffield et al. (1989)); (3) RNase protection assays (Finkelstein et al. (1990); Kinszler et al. (1991)); (4) allele-specific oligonucleotides (ASOs) (Conner et al. (1983)); (5) the use of proteins which recognize nucleotide mismatches, such as the *E. coli* mutS protein (Modrich (1991)); and, (6) allele-specific PCR (Ruano et al. (1989)). For allele-specific PCR, primers are used which hybridize at their 3' ends to a particular AGT mutation. If the particular AGT mutation is not present, an amplification product is not observed. Amplification Refractory Mutation System (ARMS) can also be used, as disclosed in Published European Patent Application No. 0332435 and in Newton et al. (1989)).

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type AGT gene coding sequence.

The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site −11 of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the AGT mRNA or gene but can be a segment of either. If the riboprobe comprises only a segment of the AGT mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al. (1988; Shenk et al. (1975; Novack et al. (1986. Alternatively, mismatches can be detected by shifts in the electrophoretic mobility of mismatched duplexes relative to matched duplexes. See, e.g., Cariello (1988. With either riboprobes or DNA probes, the cellular mRNA or DNA which might contain a mutation can be amplified using PCR before hybridization. Changes in DNA of the AGT gene can also be detected using Southern hybridization, especially if the changes are gross rearrangements, such as deletions and insertions.

DNA sequences of the AGT gene which have been amplified by use of PCR may also be screened using allele-specific probes. These probes are nucleic acid oligomers, each of which contains a region of the AGT gene sequence harboring a known mutation. For example, one oligomer may be about 30 nucleotides in length, corresponding to a portion of the AGT gene sequence. By use of a battery of such allele-specific probes, PCR amplification products can be screened to identify the presence of a previously identified mutation in the AGT gene. Hybridization of allele-specific probes with amplified AGT sequences can be performed, for example, on a nylon filter. Hybridization to a particular probe under stringent hybridization conditions indicates the presence of the same mutation in the DNA sample as in the allele-specific probe. Mutations falling outside the coding region of AGT can be detected by examining non-coding regions, such as introns and regulatory sequences near/within the AGT gene. An early indication that mutations in noncoding regions are important may come from Northern blot experiments that reveal messenger RNA molecules of abnormal size or abundance in hypertensive patients, compared to control individuals.

Alteration of AGT mRNA expression can be detected by any techniques known in the art. These include Northern blot analysis, PCR amplification and RNase protection. Diminished mRNA expression indicates an alteration of the wild-type ATG gene. Alteration of wild-type AGT genes can also be detected by screening for alteration of wild-type angiotensinogen. For example, monoclonal antibodies immunoreactive with angiotensinogen can be used to screen a tissue. Lack of cognate antigen would indicate a AGT gene mutation. Antibodies specific for products of mutant alleles could also be used to detect mutant AGT gene product. Such immunological assays can be done in any convenient formats known in the art. These include Western blots, immunohistochemical assays and ELISA assays. Any means for detecting an altered angiotensinogen can be used to detect alteration of wild-type AGT genes. Finding a mutant AGT gene product indicates alteration of a wild-type AGT gene. Further details of a suitable PCR method are described in the examples in U.S. Pat. No. 5,374,525 and U.S. patent application Ser. No. 09/106,216. The AGT alleles can be screened for the variants described herein, as well as other variants using these techniques or those techniques known in the art.

The present invention is further detailed in the following Examples, which are offered by way of illustration and are not intended to limit the invention in any manner. Standard techniques well known in the art or the techniques specifically described below, or in U.S. Pat. No. 5,374,525 or in U.S. patent application Ser. No. 09/106,216 (or corresponding International Patent Application No. PCT/US99/08280) are utilized.

EXAMPLE 1

Identification of the T/C(67) Variant

Using techniques similar to those described in U.S. Pat. No. 5,374,525 and U.S. patent application Ser. No. 09/106,216, the sequence of cloned AGT genes were examined to determine the presence of AGT variants. This sequence analysis identified an additional molecular variant in the AGT gene. This variant occurs in the first intron of the gene. The variant is characterized by the presence of either thymine (T) or cytosine (C) at position 67 relative to the initiation of transcription, such as shown in SEQ ID NO: 4.

EXAMPLE 2

Frequency and Association Patterns in Caucasians

The T/C(67) variant was examined in a sample of unrelated Caucasians that define the CEPH panel. As shown in Tables 1A and 1B, the polymorphism is common, and disequilibrium with T325 is quasi-complete; over 90% of the T325 alleles exhibit C(67), and likewise about 90% of M235 alleles exhibit T(67).

TABLE 1A

Distribution of Genotypes Defined by
M/T235 and T/C (67) Polymorphisms

| Genotype | Observed | Expected | $\chi^2$ |
|---|---|---|---|
| MM-TT | 44 | 44.75 | 0.01 |
| MM-TC | 7 | 5.59 | 0.36 |
| MM-CC | 1 | 0.17 | 3.90 |
| MT-TT | 5 | 3.77 | 0.40 |
| MT-TC | 48 | 49.15 | 0.03 |
| TT-TC | 1 | 2.06 | 0.55 |
| TT-CC | 16 | 13.37 | 0.52 |
| TOTAL | 122 | 122.00 | 8.90 |

TABLE 1B

Haplotype Frequencies Estimated
from Genotypic Data of Table 1A

| Haplotype | Frequency |
|---|---|
| M-T | 0.606 |
| M-C | 0.038 |
| T-T | 0.026 |
| T-C | 0.331 |
| TOTAL | 1.000 |

EXAMPLE 3

Interaction with Nuclear Proteins

When double-stranded DNA oligonucleotides are incubated with nuclear extracts from either liver (HepG2 cells) or embryonal kidney (293 cells), specific DNA-protein interactions are revealed through gel retardation assays (FIG. 2A). Competitive binding studies reveal that the TC(67) polymorphism affects the relative DNA affinity of the retarded complex (FIG. 2B). These data suggest that a nuclear protein can engage into specific interaction with a segment of the AGT spanning position 657, and that the T/C(67) polymorphism may differentially affect this interaction.

EXAMPLE 4

Promoter Activity

Interactions between nuclear proteins and DNA in promoter regions of genes may affect their transcriptional activity. To test the possible effect of T/C(67) polymorphism on AGT transcription, segments of the AGT promoter with all combinations of three common diallelic polymorphisms, T/C(−20), G/A(−6), and T/C(67), were expressed in cultured cells. Our data suggest that all three polymorphisms exert a significant effect on transcription activity in vitro (Tables 2A and 2B, Tables 3A and 3B). It follows that T/C(67) may be functionally relevant in blood pressure regulation and in the development of essential hypertension in humans.

TABLE 2A

Transactivation Experiments in HepG2 Cells:
Estimation of Variance Components/Tests of Significance

| Effect | Sum of Seq. | d.f. | Mean Sq. | F | Signif. | Power |
|---|---|---|---|---|---|---|
| v20 | 35.53 | 1 | 35.53 | 153.52 | 0.000 | 1.00 |
| v6 | 4.36 | 1 | 4.36 | 18.86 | 0.000 | 0.99 |
| v67 | 77.58 | 1 | 77.58 | 335.20 | 0.000 | 1.00 |
| v20*v6 | 1.76 | 1 | 1.76 | 7.62 | 0.006 | 0.78 |
| v6*v67 | 2.71 | 1 | 2.71 | 11.69 | 0.001 | 0.93 |
| v20*v67 | 0.67 | 1 | 0.67 | 2.86 | 0.093 | 0.39 |
| v20*v6*v67 | 0.39 | 1 | 0.39 | 1.69 | 0.195 | 0.25 |
| residuals | 37.03 | 160 | 0.23 | | | |

TABLE 2B

Transactivation Experiments in HepG2 Cells: Estimated Effects

| Polymorphism | Allele | Mean | S.E.M. | S.D. | Δ(S.D.) |
|---|---|---|---|---|---|
| v20 | C | 0.52 | .052 | 0.47 | 1.96 |
| | A | −0.40 | .052 | 0.47 | |
| v6 | G | 0.22 | .052 | 0.47 | 0.68 |
| | A | −0.11 | .052 | 0.47 | |
| v67 | T | 0.74 | .052 | 0.47 | 2.89 |
| | C | −0.62 | .052 | 0.47 | |

NOTE: All eight haplotypes generated by combination of the three diallelic polymorphisms were reproduced in AGT promoter segments spanning −70 to +90 fused to the Luciferase reporter gene. All transfections were performed in parallel and in triplicates, and seven independent experiments were conducted using two sets of independent plasmid preparations. Reporter activities were expressed relative to internal transfection controls, log-transformed, and standardized within experiments before analysis.

TABLE 3A

Transactivation Experiments in 293 Cells:
Estimation of Variance Components and Tests of Significance

| Effect | Sum of Seq. | d.f. | Mean Sq. | F | Signif. | Power |
|---|---|---|---|---|---|---|
| v20 | 69.84 | 1 | 69.84 | 131.55 | 0.000 | 1.00 |
| v6 | 6.36 | 1 | 6.36 | 11.99 | 0.001 | 0.93 |
| v67 | 20.44 | 1 | 20.44 | 38.50 | 0.000 | 1.00 |
| v20*v6 | 5.32 | 1 | 5.32 | 10.02 | 0.002 | 0.88 |
| v6*v67 | 1.70 | 1 | 1.70 | 3.21 | 0.075 | 0.43 |
| v20*v67 | 0.00 | 1 | 0.00 | 0.01 | 0.941 | 0.05 |
| v20*v6*v67 | 3.15 | 1 | 3.15 | 5.93 | 0.016 | 0.68 |
| residuals | 123.18 | 160 | 123.18 | | | |

TABLE 3B

Transactivation Experiments in 293 Cells: Estimated Effects

| Polymorphism | Allele | Mean | S.E.M. | S.D. | Δ(S.D.) |
|---|---|---|---|---|---|
| v20 | C | 0.54 | .067 | 0.73 | 1.47 |
| | A | −0.54 | .067 | 0.73 | |
| v6 | G | 0.17 | .067 | 0.73 | 0.44 |
| | A | −0.17 | .067 | 0.73 | |
| v67 | T | 0.29 | .067 | 0.73 | 0.79 |
| | C | −0.29 | .067 | 0.73 | |

NOTE: All eight haplotypes generated by combination of the three diallelic polymorphisms were reproduced in AGT promoter segments spanning −70 to +90 fused to the Luciferase reporter gene. All transfections were performed in parallel and in triplicates, and 10 independent experiments were conducted using two sets of independent plasmid preparations. Reporter activities were expressed relative to internal transfection controls, log-transformed, and standardized within experiments before analysis.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Arnal, J. F., et al. (1991). *Am. J. Med* 90:17–22.

Blackwelder, W. C. and Elston, R. C. (1985). *Genet. Epidemiol.* 2:85–97.

Bishop, D. T. and Williamson, J. A. (1990). *Am. J. Hum. Genet.* 46:254–265.

Brown, A. J., et al. (1981). *Am. J. Physiol.* 241:H381–H388.

Cain, M. D., et al. (1971). *J. Clin. Endocrinol.* 33:671–676.

Campbell, D. J., and Habener, J. F. (1986). *J. Clin. Invest.* 78:1427–1431.

Cariello (1988). *Human Genetics* 42:726.

Clauser, E., et al. (1989). *Am. J. Hypertens.* 2:403–410.

Conner, B. J., et al. (1983). *Proc. Natl. Acad. Sci. USA.* 80:278–282.

Cotton, et al. (1988). *Proc. Natl. Acad. Sci. USA* 85:4397.

Fasola, A. F., et al. (1968). *J. Appl. Physiol.* 25:410–415.

Finkelstein, J., et al. (1990). *Genomics* 7: 167–172.

Fukamizu, A., et al. (1990). *J. Biol. Chem.* 265:7576–7582.

Gaillard, I., et al. (1989). *DNA* 8:87–99.

Gardes, J., et al. (1982). *Hypertension* 4:185–189.

Gould, A. B., et al. (1971). *Cardiovasc. Res.* 5:86–89.

Hall, J. E., and Guyton, A. C. (1990). In: *Hypertension: Pathophysiology Diagnosis and Management,* Laragh, J. H. and Brenner, B. M., eds., (Raven Press, Ltd., NY), pp. 1105–1129.

Jeunemaitre, X., et al. (1992). *Cell* 71:169–178.

Jeunemaitre, X., et al. (1993). *J. Hyperten.* 11(Supp. 5):S80–S81.

Jeunemaitre, X., et al. (1997). *Am. J. Hum. Genet.* 60:1448–1460.

Kimura, S., et al. (1992). *EMBO J.* 11:821 827.

Kinszler, K. W., et al. (1991). *Science* 251:1366–1370.

Lalouel, J. M. (1990). In: *Drugs Affecting Lipid Metabolism,* A. M. Gotto and L. C. Smith (eds.), Elsevier Science Publishers, Amsterdam, pp. 11–21.

Lander, E. S., and Botstein, D. (1986). *Cold Spring Harbor Symp. Quant. Biol.* 51:46–61.

Lander, E. S., and Botstein, D. (1989). *Genetics* 121:185 199.

Lathrop, G. M., and Lalouel, J. M. (1991). In: *Handbook of Statistics,* Vol. 8 (Elsevier Science Publishers, Amsterdam), pp. 81–123.

Menard, J., and Catt, K. J. (1973). *Endocrinology* 92:1382–1388.

Menard, J., et al. (1991). *Hypertension* 18:705–706.

Modrich, P. (1991). *Ann. Rev. Genet.* 25:229–253.

Newton, C. R., et al. (1989). *Nucl. Acids Res.* 17:2503–2516.

Novack, et al. (1986). *Proc. Nat. Acad. Sci. USA* 83:586.

Ohkubo, H., et al. (1990). *Proc. Nat. Acad. Sci. USA* 87:5153–5157.

Orita, M., et al. (1989). *Proc. Nat. Acad. Sci. USA* 86:2766–2770.

Pratt, R. E., et al. (1989). *Am. J. Physiol.* 256:F469–F474.

Ruano & Kidd (1989). *Nucl. Acids Res.* 17:8392.

Rust, S., et al. (1993). *Nucl. Acids Res.* 21:3623–3629.

Sealey, J. E., and Laragh, J. H. (1990). In: *Hypertension: Pathophysiology. Diagnosis and Management,* J. H. Laragh and B. M. Brenner, eds. (Raven Press, NY), pp. 1287–1317.

Sheffield, V. C., et al. (1989). *Proc. Nat. Acad. Sci. USA* 86: 232–236.

Shenk, et al. (1975). *Proc. Nat. Acad Sci. USA* 72:989.

Suarez, B. K., and Van Eerdewegh, P. (1984). *Am. J Med. Genet.* 18:135 146.

Walker, W. G., et al. (1979). *Hypertension* 1:287 291.

Ward, R. (1990). In: *Hypertension: Pathophysiology, Diagnosis and Management,* Laragh, J. H. and Brenner, B. M., eds., (Raven Press, NY), pp. 81–100.

Wartell, R. M., et al. (1990). *Nucl. Acids Res.* 18:2699–2705.

Watt, G. C. M., et al. (1992). *J. Hypertens.* 10:473–482.

White, R. L., and Lalouel, J. M. (1987). In: *Advances in Human Genetics,* Vol. 16, H. Harris and K. Hirschhorn, eds. (Plenum Press, NY), pp. 121–128.

Yongue, B. G., et al. (1991). *Hypertension* 17:485–491.

U.S. Pat. No. 5,374,525

U.S. Pat. No. 5,763,168

U.S. patent application Ser. No. 09/106,216

PCT Patent Application No. PCT/US99/08280

Published European Patent No. 0332435

What is claimed is:

1. A method for determining the predisposition of an individual to hypertension which comprises analyzing the DNA sequence of the angiotensinogen (AGT) gene of said individual for the variant T67C, whereby the presence of the variant T67C in an individual is indicative of a predisposition of said individual to hypertension.

2. The method of claim 1 wherein the genomic sequence of the AGT gene of said human is analyzed.

3. The method of claim 1 wherein a part of the genomic sequence of the AGT gene of said human is analyzed.

4. The method of claim 1 wherein said analysis is carried out by hybridization.

5. The method of claim 4 wherein said hybridization is with an allele-specific oligonucleotile probe.

6. The method of claim 1 wherein said analysis is carried out by sequence analysis.

7. The method of claim 1 wherein said analysis is carried out by SSCP analysis.

8. The method of claim 1, wherein said predisposition is a predisposition to essential hypertension.

9. The method of claim 1, wherein said predisposition is a predisposition to pregnancy-induced hypertension.

10. A nucleic acid probe which specifically hybridizes to the T67C angiotensinogen gene alteration.

* * * * *

SEQUENCE LISTING

```
<160> NUMBER OF SEQ ID NOS: 5

<210> SEQ ID NO 1
<211> LENGTH: 1496
<212> TYPE: DNA
<213> ORGANISM: Homo sapiens
<220> FEATURE:
<221> NAME/KEY: CDS
<222> LOCATION: (39)..(1493)

<400> SEQUENCE: 1
agaagctgcc gttgttctgg gtactacagc agaagggt atg cgg aag cga gca ccc      56
                                         Met Arg Lys Arg Ala Pro
                                          1               5
```

-continued

| | | |
|---|---|---|
| cag tct gag atg gct cct gcc ggt gtg agc ctg agg gcc acc atc ctc<br>Gln Ser Glu Met Ala Pro Ala Gly Val Ser Leu Arg Ala Thr Ile Leu<br>             10               15             20 | 104 |
| tgc ctc ctg gcc tgg gct ggc ctg gct gca ggt gac cgg gtg tac ata<br>Cys Leu Leu Ala Trp Ala Gly Leu Ala Ala Gly Asp Arg Val Tyr Ile<br>          25               30             35 | 152 |
| cac ccc ttc cac ctc gtc atc cac aat gag agt acc tgt gag cag ctg<br>His Pro Phe His Leu Val Ile His Asn Glu Ser Thr Cys Glu Gln Leu<br>40               45              50 | 200 |
| gca aag gcc aat gcc ggg aag ccc aaa gac ccc acc ttc ata cct gct<br>Ala Lys Ala Asn Ala Gly Lys Pro Lys Asp Pro Thr Phe Ile Pro Ala<br>55               60              65             70 | 248 |
| cca att cag gcc aag aca tcc cct gtg gat gaa aag gcc cta cag gac<br>Pro Ile Gln Ala Lys Thr Ser Pro Val Asp Glu Lys Ala Leu Gln Asp<br>          75               80              85 | 296 |
| cag ctg gtg cta gtc gct gca aaa ctt gac acc gaa gac aag ttg agg<br>Gln Leu Val Leu Val Ala Ala Lys Leu Asp Thr Glu Asp Lys Leu Arg<br>             90               95            100 | 344 |
| gcc gca atg gtc ggg atg ctg gcc aac ttc ttg ggc ttc cgt ata tat<br>Ala Ala Met Val Gly Met Leu Ala Asn Phe Leu Gly Phe Arg Ile Tyr<br>          105              110            115 | 392 |
| ggc atg cac agt gag cta tgg ggc gtg gtc cat ggg gcc acc gtc ctc<br>Gly Met His Ser Glu Leu Trp Gly Val Val His Gly Ala Thr Val Leu<br>120               125             130 | 440 |
| tcc cca acg gct gtc ttt ggc acc ctg gcc tct ctc tat ctg gga gcc<br>Ser Pro Thr Ala Val Phe Gly Thr Leu Ala Ser Leu Tyr Leu Gly Ala<br>135               140             145            150 | 488 |
| ttg gac cac aca gct gac agg cta cag gca atc ctg ggt gtt cct tgg<br>Leu Asp His Thr Ala Asp Arg Leu Gln Ala Ile Leu Gly Val Pro Trp<br>             155             160            165 | 536 |
| aag gac aag aac tgc acc tcc cgg ctg gat gcg cac aag gtc ctg tct<br>Lys Asp Lys Asn Cys Thr Ser Arg Leu Asp Ala His Lys Val Leu Ser<br>          170              175            180 | 584 |
| gcc ctg cag gct gta cag ggc ctg cta gtg gcc cag ggc agg gct gat<br>Ala Leu Gln Ala Val Gln Gly Leu Leu Val Ala Gln Gly Arg Ala Asp<br>185               190             195 | 632 |
| agc cag gcc cag ctg ctg ctg tcc acg gtg gtg ggc gtg ttc aca gcc<br>Ser Gln Ala Gln Leu Leu Leu Ser Thr Val Val Gly Val Phe Thr Ala<br>200               205             210 | 680 |
| cca ggc ctg cac ctg aag cag ccg ttt gtg cag ggc ctg gct ctc tat<br>Pro Gly Leu His Leu Lys Gln Pro Phe Val Gln Gly Leu Ala Leu Tyr<br>215               220             225            230 | 728 |
| acc cct gtg gtc ctc cca cgc tct ctg gac ttc aca gaa ctg gat gtt<br>Thr Pro Val Val Leu Pro Arg Ser Leu Asp Phe Thr Glu Leu Asp Val<br>             235             240            245 | 776 |
| gct gct gag aag att gac agg ttc atg cag gct gtg aca gga tgg aag<br>Ala Ala Glu Lys Ile Asp Arg Phe Met Gln Ala Val Thr Gly Trp Lys<br>          250              255            260 | 824 |
| act ggc tgc tcc ctg atg gga gcc agt gtg gac agc acc ctg gct ttc<br>Thr Gly Cys Ser Leu Met Gly Ala Ser Val Asp Ser Thr Leu Ala Phe<br>265               270             275 | 872 |
| aac acc tac gtc cac ttc caa ggg aag atg aag ggc ttc tcc ctg ctg<br>Asn Thr Tyr Val His Phe Gln Gly Lys Met Lys Gly Phe Ser Leu Leu<br>280               285             290 | 920 |
| gcc gag ccc cag gag ttc tgg gtg gac aac agc acc tca gtg tct gtt<br>Ala Glu Pro Gln Glu Phe Trp Val Asp Asn Ser Thr Ser Val Ser Val<br>295               300             305            310 | 968 |
| ccc atg ctc tct ggc atg ggc acc ttc cag cac tgg agt gac atc cag<br>Pro Met Leu Ser Gly Met Gly Thr Phe Gln His Trp Ser Asp Ile Gln<br>          315              320            325 | 1016 |

-continued

```
gac aac ttc tcg gtg act gaa gtg ccc ttc act gag agc gcc tgc ctg     1064
Asp Asn Phe Ser Val Thr Glu Val Pro Phe Thr Glu Ser Ala Cys Leu
            330                 335                 340 ctg ctg atc cag cct cac tat gcc tct gac ctg gac aag gtg gag ggt     1112
Leu Leu Ile Gln Pro His Tyr Ala Ser Asp Leu Asp Lys Val Glu Gly
            345                 350                 355 ctc act ttc cag caa aac tcc ctc aac tgg atg aag aaa ctg tct ccc     1160
Leu Thr Phe Gln Gln Asn Ser Leu Asn Trp Met Lys Lys Leu Ser Pro
            360                 365                 370 cgg acc atc cac ctg acc atg ccc caa ctg gtg ctg caa gga tct tat     1208
Arg Thr Ile His Leu Thr Met Pro Gln Leu Val Leu Gln Gly Ser Tyr
375                 380                 385                 390 gac ctg cag gac ctg ctc gcc cag gct gag ctg ccc gcc att ctg cac     1256
Asp Leu Gln Asp Leu Leu Ala Gln Ala Glu Leu Pro Ala Ile Leu His
            395                 400                 405 acc gag ctg aac ctg caa aaa ttg agc aat gac cgc atc agg gtg ggg     1304
Thr Glu Leu Asn Leu Gln Lys Leu Ser Asn Asp Arg Ile Arg Val Gly
            410                 415                 420 gag gtg ctg aac agc att ttt ttt gag ctt gaa gcg gat gag aga gag     1352
Glu Val Leu Asn Ser Ile Phe Phe Glu Leu Glu Ala Asp Glu Arg Glu
            425                 430                 435 ccc aca gag tct acc caa cag ctt aac aag cct gag gtc ttg gag gtg     1400
Pro Thr Glu Ser Thr Gln Gln Leu Asn Lys Pro Glu Val Leu Glu Val
            440                 445                 450 acc ctg aac cgc cca ttc ctg ttt gct gtg tat gat caa agc gcc act     1448
Thr Leu Asn Arg Pro Phe Leu Phe Ala Val Tyr Asp Gln Ser Ala Thr
455                 460                 465                 470 gcc ctg cac ttc ctg ggc cgc gtg gcc aac ccg ctg agc aca gca tga     1496
Ala Leu His Phe Leu Gly Arg Val Ala Asn Pro Leu Ser Thr Ala
            475                 480                 485

<210> SEQ ID NO 2
<211> LENGTH: 485
<212> TYPE: PRT
<213> ORGANISM: Homo sapiens

<400> SEQUENCE: 2

Met Arg Lys Arg Ala Pro Gln Ser Glu Met Ala Pro Ala Gly Val Ser
  1               5                  10                  15

Leu Arg Ala Thr Ile Leu Cys Leu Leu Ala Trp Ala Gly Leu Ala Ala
                 20                  25                  30

Gly Asp Arg Val Tyr Ile His Pro Phe His Leu Val Ile His Asn Glu
             35                  40                  45

Ser Thr Cys Glu Gln Leu Ala Lys Ala Asn Ala Gly Lys Pro Lys Asp
     50                  55                  60

Pro Thr Phe Ile Pro Ala Pro Ile Gln Ala Lys Thr Ser Pro Val Asp
 65                  70                  75                  80

Glu Lys Ala Leu Gln Asp Gln Leu Val Leu Val Ala Ala Lys Leu Asp
                 85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160
```

```
Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
                180                 185                 190

Ala Gln Gly Arg Ala Asp Ser Gln Ala Gln Leu Leu Leu Ser Thr Val
                195                 200                 205

Val Gly Val Phe Thr Ala Pro Gly Leu His Leu Lys Gln Pro Phe Val
                210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
                260                 265                 270

Asp Ser Thr Leu Ala Phe Asn Thr Tyr Val His Phe Gln Gly Lys Met
                275                 280                 285

Lys Gly Phe Ser Leu Leu Ala Glu Pro Gln Glu Phe Trp Val Asp Asn
                290                 295                 300

Ser Thr Ser Val Ser Val Pro Met Leu Ser Gly Met Gly Thr Phe Gln
305                 310                 315                 320

His Trp Ser Asp Ile Gln Asp Asn Phe Ser Val Thr Glu Val Pro Phe
                325                 330                 335

Thr Glu Ser Ala Cys Leu Leu Leu Ile Gln Pro His Tyr Ala Ser Asp
                340                 345                 350

Leu Asp Lys Val Glu Gly Leu Thr Phe Gln Gln Asn Ser Leu Asn Trp
                355                 360                 365

Met Lys Lys Leu Ser Pro Arg Thr Ile His Leu Thr Met Pro Gln Leu
                370                 375                 380

Val Leu Gln Gly Ser Tyr Asp Leu Gln Asp Leu Leu Ala Gln Ala Glu
385                 390                 395                 400

Leu Pro Ala Ile Leu His Thr Glu Leu Asn Leu Gln Lys Leu Ser Asn
                405                 410                 415

Asp Arg Ile Arg Val Gly Glu Val Leu Asn Ser Ile Phe Phe Glu Leu
                420                 425                 430

Glu Ala Asp Glu Arg Glu Pro Thr Glu Ser Thr Gln Gln Leu Asn Lys
                435                 440                 445

Pro Glu Val Leu Glu Val Thr Leu Asn Arg Pro Phe Leu Phe Ala Val
                450                 455                 460

Tyr Asp Gln Ser Ala Thr Ala Leu His Phe Leu Gly Arg Val Ala Asn
465                 470                 475                 480

Pro Leu Ser Thr Ala
                485

<210> SEQ ID NO 3
<211> LENGTH: 130
<212> TYPE: DNA
<213> ORGANISM: Homo sapiens
<220> FEATURE:
<221> NAME/KEY: misc_feature
<222> LOCATION: (33)
<223> OTHER INFORMATION: Transcriptional start site according to
      Gaillard et al., DNA 8:87-99 (1989).
<220> FEATURE:
<221> NAME/KEY: misc_feature
<222> LOCATION: (96)
<223> OTHER INFORMATION: C at position 96 is an additional base compared
      to the sequence reported by Gaillard et al., DNA
      8:87-99 (1989).
```

```
<220> FEATURE:
<221> NAME/KEY: misc_feature
<222> LOCATION: (99)
<223> OTHER INFORMATION: C polymorphism at postion 99 is associated with
      hypertension.
<220> FEATURE:
<221> NAME/KEY: misc_feature
<222> LOCATION: (33)..(130)
<223> OTHER INFORMATION: Sequence of exon 1 and part of intron 1
      according to Gaillard et al., DNA 8:87-99 (1989) with
      additional nucleotide as noted above.

<400> SEQUENCE: 3
tataaatagg gcatcgtgac ccggccgggg gaagaagctg ccgttgttct gggtactaca      60
gcagaaggta agcgggggcc ccctcagctc cttctcggtc ttgtctctct caggatgtaa     120
ctgagctgtg                                                            130

<210> SEQ ID NO 4
<211> LENGTH: 98
<212> TYPE: DNA
<213> ORGANISM: Homo sapiens
<220> FEATURE:
<221> NAME/KEY: misc_feature
<222> LOCATION: (1)
<223> OTHER INFORMATION: Transcriptional start site according to
      Gaillard et al., DNA 8:87-99 (1989).
<220> FEATURE:
<221> NAME/KEY: misc_feature
<222> LOCATION: (64)
<223> OTHER INFORMATION: C at position 64 is additional base compared to
      sequence according to Gaillard et al., DNA 8:87-99
      (1989).
<220> FEATURE:
<221> NAME/KEY: misc_feature
<222> LOCATION: (67)
<223> OTHER INFORMATION: C polymorphism at position 67 is associated
      with hypertension.
<220> FEATURE:
<221> NAME/KEY: misc_feature
<222> LOCATION: (1)..(98)
<223> OTHER INFORMATION: Sequence of exon 1 and part of intron 1
      according to Gaillard et al., DNA 8:87-99 (1989) with
      additional nucleotide as noted above.

<400> SEQUENCE: 4
agaagctgcc gttgttctgg gtactacagc agaaggtaag cggggccccc ctcagctcct      60
tctcggtctt gtctctctca ggatgtaact gagctgtg                              98

<210> SEQ ID NO 5
<211> LENGTH: 62
<212> TYPE: DNA
<213> ORGANISM: Homo sapiens
<220> FEATURE:
<221> NAME/KEY: misc_feature
<222> LOCATION: (1)..(62)
<223> OTHER INFORMATION: Sequence of exon 1 and part of intron 1
      according to Gaillard et al., DNA 8:87-99 (1989) with
      additional nucleotide in accordance with
      invention.

<400> SEQUENCE: 5
taagcggggg cccctcagc tccttctcgg tcttgtctct ctcaggatgt aactgagctg       60
tg                                                                    62
```